US 6,730,090 B2

(12) United States Patent
Orbay et al.

(10) Patent No.: US 6,730,090 B2
(45) Date of Patent: May 4, 2004

(54) FIXATION DEVICE FOR METAPHYSEAL LONG BONE FRACTURES

(75) Inventors: Jorge L. Orbay, Miami, FL (US); Javier Castañeda, Miami, FL (US)

(73) Assignee: Hand Innovations, Inc., Miami, FL (US)

( * ) Notice: Subject to any disclaimer, the term of this patent is extended or adjusted under 35 U.S.C. 154(b) by 100 days.

(21) Appl. No.: 10/159,611

(22) Filed: May 30, 2002

(65) Prior Publication Data

US 2002/0143337 A1 Oct. 3, 2002

Related U.S. Application Data

(63) Continuation-in-part of application No. 09/735,228, filed on Dec. 12, 2000, now Pat. No. 6,440,135, and a continuation-in-part of application No. 09/524,058, filed on Mar. 13, 2000, now Pat. No. 6,364,882, and a continuation-in-part of application No. 09/495,854, filed on Feb. 1, 2000, now Pat. No. 6,358,250.

(51) Int. Cl.⁷ .............................................. A61B 17/80
(52) U.S. Cl. .................................................. 606/69
(58) Field of Search ........................... 606/60, 67–72

(56) References Cited

U.S. PATENT DOCUMENTS

| | | | |
|---|---|---|---|
| 3,025,853 A | 3/1962 | Mason ........................ 128/92 |
| 3,939,498 A | 2/1976 | Lee et al. .................... 3/1.913 |
| 4,135,507 A | 1/1979 | Harris ......................... 128/92 |
| 4,153,953 A | 5/1979 | Grobbelaar ................. 3/1.913 |
| 4,172,452 A | 10/1979 | Forte et al. .................. 128/923 |
| 4,483,335 A | 11/1984 | Tornier .................. 128/92 BC |
| 4,506,662 A | 3/1985 | Anapliotis .................... 128/92 |
| 4,776,330 A | 10/1988 | Chapman et al. ............. 128/92 |
| 4,794,919 A | 1/1989 | Nilsson ........................ 128/92 |
| 4,923,471 A | 5/1990 | Morgan ........................ 923/16 |
| 5,013,314 A | 5/1991 | Firica et al. ................... 606/64 |
| 5,035,697 A | 7/1991 | Frigg ............................ 606/67 |
| 5,304,180 A | 4/1994 | Slocum ........................ 606/69 |
| 5,352,229 A | * 10/1994 | Goble et al. .................. 606/72 |
| 5,356,410 A | 10/1994 | Pennig ......................... 606/62 |
| 5,382,248 A | 1/1995 | Jacobson et al. ............. 606/60 |
| 5,458,654 A | 10/1995 | Tepic ........................... 623/23 |
| 5,472,444 A | 12/1995 | Huebner et al. .............. 606/64 |
| 5,484,438 A | 1/1996 | Pennig ......................... 606/64 |
| 5,536,127 A | 7/1996 | Pennig ....................... 411/413 |
| 5,591,168 A | 1/1997 | Judet et al. ................... 606/65 |
| 5,603,715 A | 2/1997 | Kessler ......................... 606/63 |
| 5,662,655 A | 9/1997 | Laboureau et al. ........... 606/75 |
| 5,665,087 A | 9/1997 | Huebner ....................... 606/65 |
| 5,709,682 A | 1/1998 | Medoff ......................... 606/60 |
| 5,718,705 A | 2/1998 | Sammarco .................... 606/69 |
| 5,766,174 A | 6/1998 | Perry ............................ 606/62 |
| 5,776,194 A | 7/1998 | Mikol et al. ................... 623/16 |
| 5,931,839 A | 8/1999 | Medoff ......................... 606/69 |

(List continued on next page.)

FOREIGN PATENT DOCUMENTS

CH              0 451 427 A1     5/1990     ............. A61F/2/36

Primary Examiner—Kevin Shaver
Assistant Examiner—Michael B. Priddy
(74) Attorney, Agent, or Firm—Gordon & Jacobson, P.C.

(57) ABSTRACT

A fixation device is provided which includes a proximal nail portion and a distal plate portion. The nail portion includes a flexible tapered section, and a rigid distal section larger in diameter and is adapted to be inserted into a medullary canal of a fractured bone. The plate portion has a low, narrow profile and includes three longitudinally displaced peg holes, each of which is adapted to orient a peg in a different orientation from the others. The plate portion is adapted to be positioned on the outside of a fractured bone when the nail portion is within the medullary canal. The device provides the benefits of both an intramedullary nail and a bone plate in a single device. The fixation device permits a minimally invasive treatment of the metaphyseal fractures that may otherwise be undertreated.

38 Claims, 5 Drawing Sheets

U.S. PATENT DOCUMENTS

| | | |
|---|---|---|
| 5,938,664 A | 8/1999 | Winquist et al. ............... 606/69 |
| 5,941,878 A | 8/1999 | Medoff ......................... 606/60 |
| 5,967,046 A * | 10/1999 | Muller ........................ 101/375 |
| 6,146,384 A | 11/2000 | Lee et al. ..................... 606/73 |
| 6,231,576 B1 | 5/2001 | Frigg et al. ................... 606/62 |
| 6,248,109 B1 | 6/2001 | Stoffella ....................... 606/75 |
| 6,270,499 B1 | 8/2001 | Leu et al. ..................... 606/64 |
| 6,355,041 B1 | 3/2002 | Martin ......................... 606/62 |
| 6,379,359 B1 | 4/2002 | Dahners ....................... 606/62 |
| 6,409,768 B1 | 6/2002 | Tepic et al. ............... 623/23.27 |
| 6,527,775 B1 | 3/2003 | Warburton .................... 606/62 |
| 6,623,486 B1 * | 9/2003 | Weaver et al. ................. 606/69 |
| 2003/0105461 A1 | 6/2003 | Putnam ........................ 606/69 |

* cited by examiner

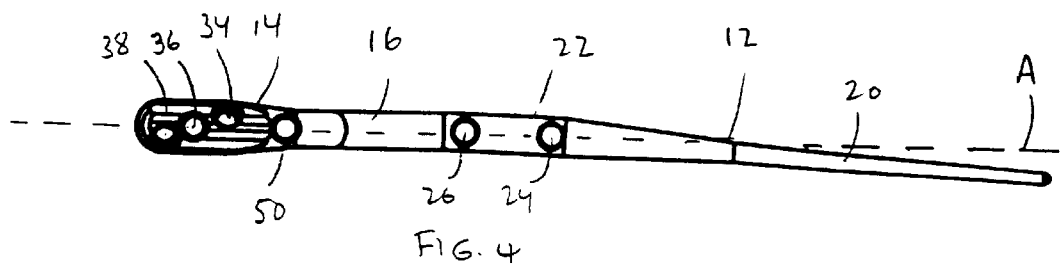
FIG. 4
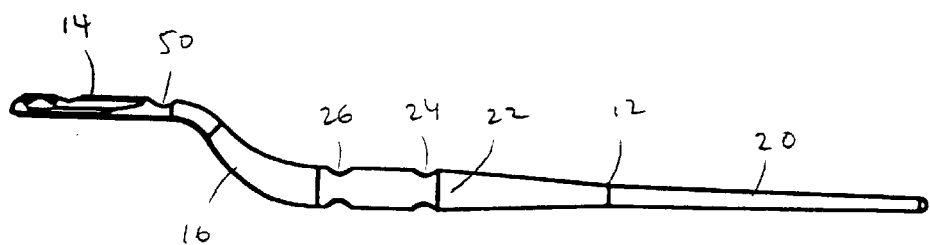
FIG. 5
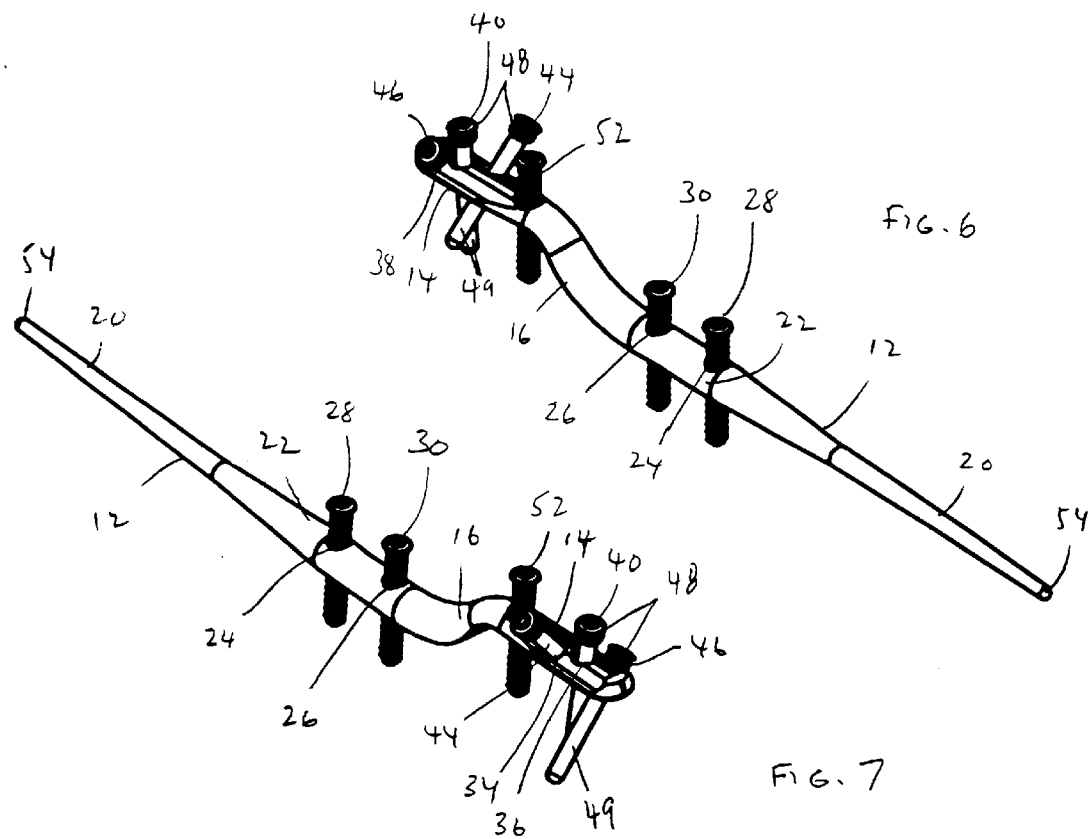
FIG. 6
FIG. 7

FIXATION DEVICE FOR METAPHYSEAL LONG BONE FRACTURES

This application is a continuation-in-part of U.S. Ser. No. 09/495,854, filed Feb. 1, 2000 now U.S. Pat. No. 6,358,250, U.S. Ser. No. 09/524,058, filed Mar. 13, 2000 now U.S. Pat. No. 6,364,882, and U.S. Ser. No. 09/735,228, filed Dec. 12, 2000 U.S. Pat. No. 6,440,135, all of which are hereby incorporated by reference herein in their entireties.

BACKGROUND OF THE INVENTION

1. Field of the Invention

This invention relates broadly to surgical devices. More particularly, this invention relates to implants for the fixation of bone fractures, particularly in long bones such as the radius and tibia.

2. State of the Art

Severe long bone fractures are often treated with plating. In plating, a relatively large incision is made at the location of the fracture, musculature and tendons are displaced from the bone to expose the bone surface, and a bone plate is fixedly attached to one or more pieces of the fractured bone in a manner which, ideally, supports and stabilizes the fracture for healing. Due to the relatively invasive nature of the procedure required to implant the plate, plating is generally reserved for fractures which cannot be treated with a less invasive method of immobilization.

Less complicated fractures are often treated with casting or wires. However, such conservative treatment may not provide the stabilization and support necessary for desirable recovery. Yet, the operative procedure of plating is often too invasive for the relative non-severity of the fracture. Moreover, conventional plating can result in tendon irritation and skin necrosis. As such, many of the less displaced fractures, and particularly metaphyseal fractures (fractures at the end of the long bones), remain undertreated.

By way of example, a Colles' fracture, which results from compressive forces being placed on the distal radius bone, and which causes backward displacement of the distal fragment and radial deviation of the hand at the wrist, is treated with a dorsal plate when there is a significant degree of displacement. However, a less-displaced Colles' fracture is commonly undertreated due to the hesitancy of physicians to prescribe operative and invasive treatment. If not properly treated, such a fracture results in permanent wrist deformity. It is therefore important to align the fracture and fixate the bones relative to each other so that proper healing may occur.

In addition, there is no minimally invasive procedure to treat fractures occurring at the metaphysis and that also provides the desired immobilization for such fractures.

Furthermore, there is no minimally invasive procedure to treat distal radius fractures that provides the stability generally obtained by more invasive procedures, such as open reduction and internal fixation.

SUMMARY OF THE INVENTION

It is therefore an object of the invention to provide a minimally invasive treatment which provides stabilization and support to long bone fractures.

It is another object of the invention to provide a minimally invasive treatment which provides stabilization and support to metaphyseal fractures.

It is a further object of the invention to provide a minimally invasive treatment which provides stabilization and support to fractures occurring at the metaphysis.

In accord with these objects, which will be discussed in detail below, a fixation device is provided which includes a proximal nail portion and a distal plate portion, preferably horizontally and vertically offset relative to the nail portion by a neck portion, e.g., such that the device preferably has a shape of an elongate 'S'. The nail portion includes a tapered end which is flexible, and a relatively rigid distal portion larger in diameter. For treatment of distal radius fractures, the distal portion of the nail portion preferably includes two cortical screw holes, and the plate portion has a low, narrow profile and includes three longitudinally displaced peg holes, each of which is adapted to orient a peg in a different orientation from the others. The plate portion also includes a screw hole intended to receive a stabilization screw.

In use, a small incision is made in the skin, and the tapered end of the nail portion of the device is introduced percutaneously through the incision and through the fracture location into the medullary canal of the bone. The plate portion of the device is then maneuvered against a surface of the bone, and a stabilization screw is introduced to drive the plate against the bone. Holes are drilled through the peg holes and into the bone, and pegs are introduced through the holes to provide stabilization and support for subchondral fragments. Optionally, cortical screws may be provided into the diaphyseal portion of the bone and into the cortical screw holes to further fixate the device.

The fixation device permits a minimally invasive treatment of long bone fractures that may otherwise be undertreated.

Additional objects and advantages of the invention will become apparent to those skilled in the art upon reference to the detailed description taken in conjunction with the provided figures.

BRIEF DESCRIPTION OF THE DRAWINGS

FIG. 4 is a top view of the fixation device of the invention;

FIG. 5 is a side elevation of the fixation device of the invention;

FIG. 6 is a proximal end top perspective view of the fixation device provided with screws and pegs;

FIG. 7 is a distal end top perspective view of the fixation device provided with screws and pegs;

DETAILED DESCRIPTION OF THE PREFERRED EMBODIMENTS

Figure 1:
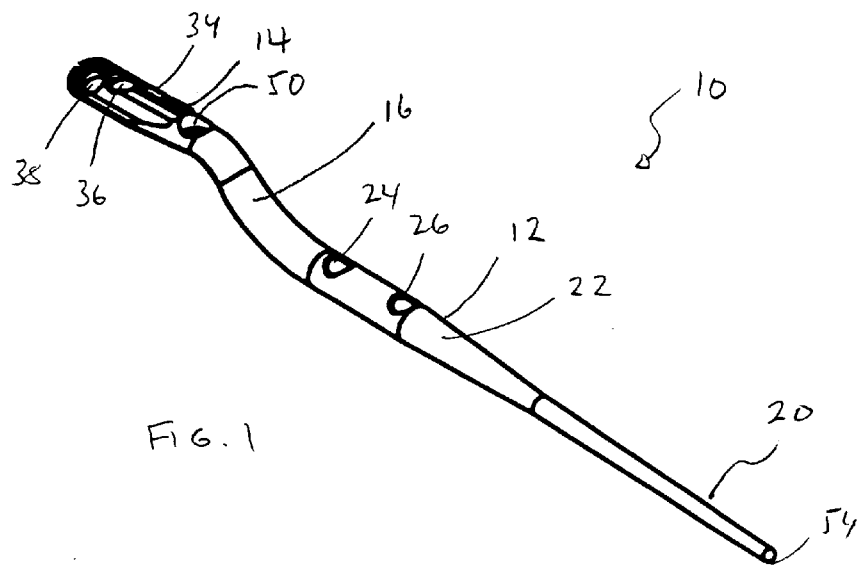
FIG. 1 is a proximal end top perspective view of the fixation device of the invention.
Figure 2:
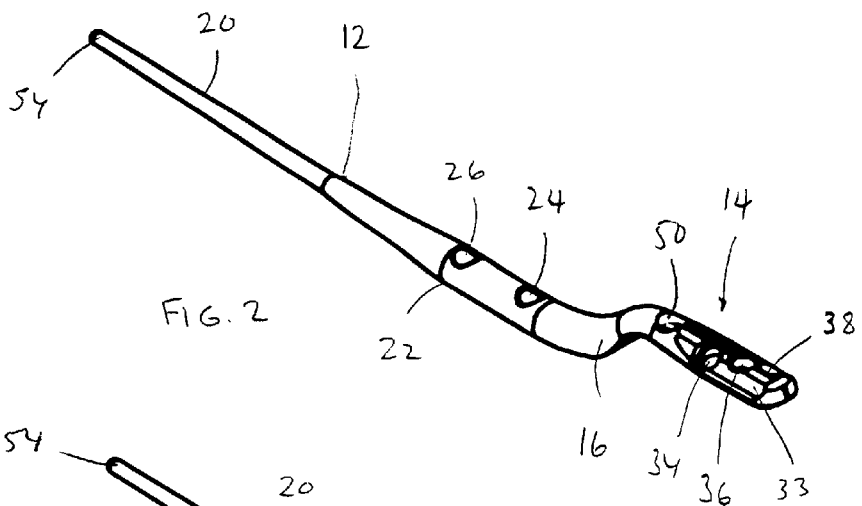
FIG. 2 is a distal end top perspective view of the fixation device of the invention.
Figure 3:
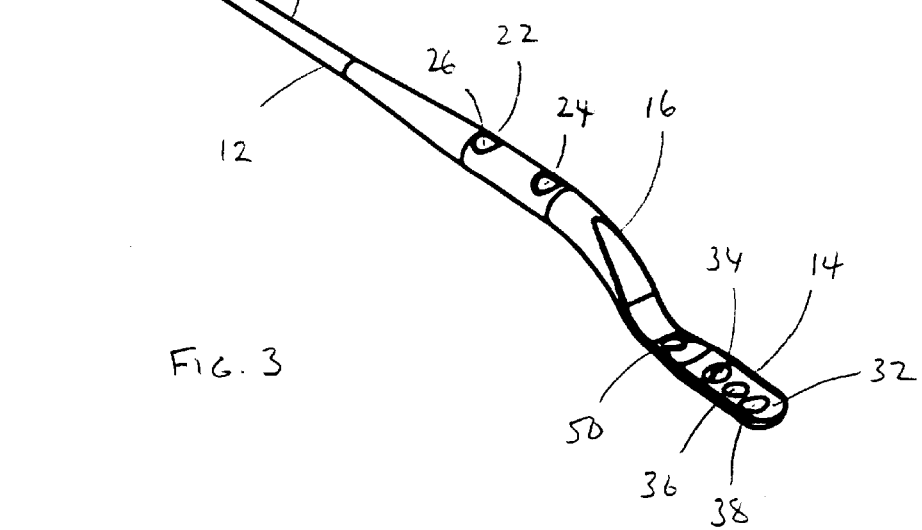
FIG. 3 is a distal end bottom perspective view of the fixation device of the invention.

Turning now to FIGS. 1 through 5, a fixation device 10 for the treatment of a fracture at an end of a long bone, i.e., a metaphyseal fracture, is provided. The device 10 is preferably made of metal, e.g., titanium or stainless steel, and includes a proximal nail portion 12 and a distal plate portion 14 that is preferably horizontally and vertically offset relative to the nail portion, e.g., by an 'S' shaped neck portion (or transition zone) 16 such that the entire device assumes a fixed elongate 'S' shape. As such, the nail portion 12 and the plate portion 14 are fixed in a parallel, but non-coaxial relationship.

The nail portion 12 is preferably substantially circular in cross section and includes a tapered flexible section 20, and a distal relatively rigid section 22 generally substantially larger in diameter. The flexible section 20 is preferably slightly skewed laterally (e.g., approximately 2° to 8°, and more preferably approximately 4°) relative to an axis A extending through the plate portion and distal portion of the rigid section 22 (FIG. 4). The rigid section 22 preferably tapers into the flexible section 20. The rigid section 22 of the nail portion 12 preferably includes two cortical screw holes 24, 26 arranged along the length of the rigid section 22 and adapted to receive cortical screws 28, 30 (FIGS. 6 and 7).

Referring to FIGS. 1 through 7, the plate portion 14 is substantially rigid and has a low and narrow profile. The plate portion 14 has a slightly concave bottom surface 32 and a slightly convex upper surface 33. The plate portion 14 also includes three longitudinally displaced, threaded peg holes 34, 36, 38, each of which-is adapted to orient a peg (preferably having a threaded head portion) in a different orientation from the others. In a preferred embodiment, the central peg hole 36 orients a central peg 40 normal to the bottom 42 of the plate portion, while the other peg holes 34 and 38 are adapted to orient pegs 44, 46 approximately forty degrees medially and laterally, respectively, relative to the central peg 40. That is, the pegs 40, 44, 46 are in a fanned arrangement. Preferably the pegs 40, 44, and 46 are also oriented perpendicular relative to the longitudinal axis of both the nail and plate portions 12, 14. The plate portion 14 also includes a screw hole 50 adjacent the neck portion 16 that is adapted to receive a stabilization screw 52.

Figure 8:
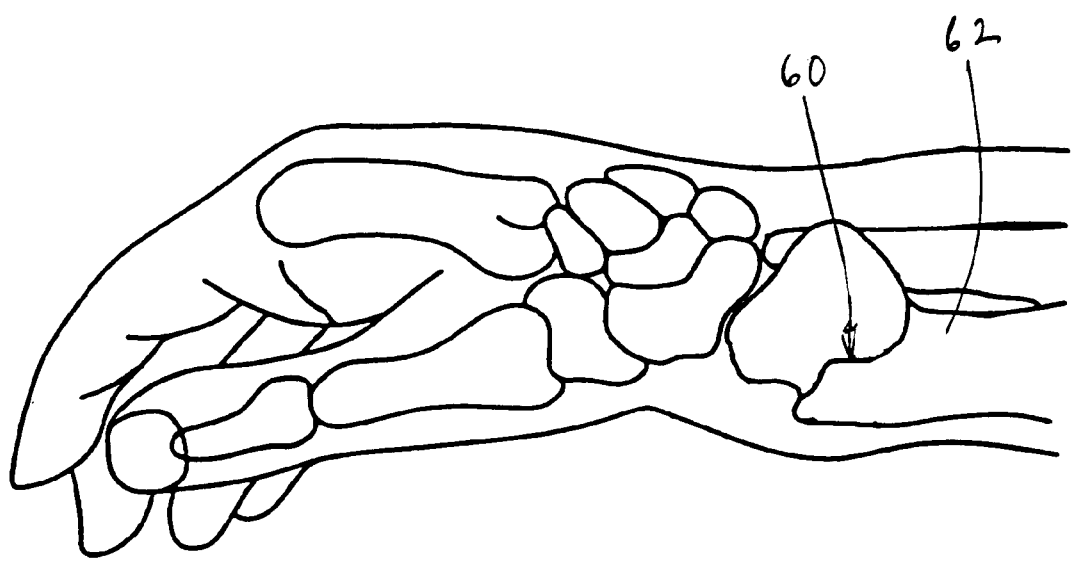
FIG. 8 is a schematic view of a distal radius fracture.
Figure 9:
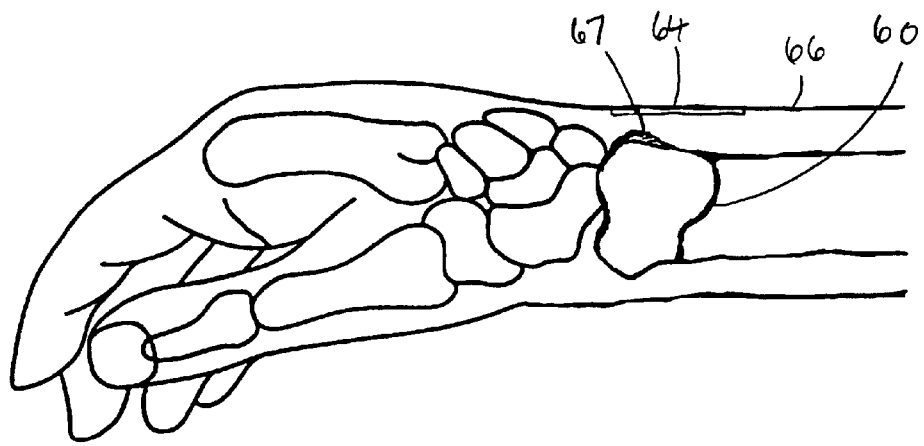
FIGS. 9 through 14 illustrate the method of the invention for treating a metaphyseal fracture, particularly at the distal radius.
Figure 10:
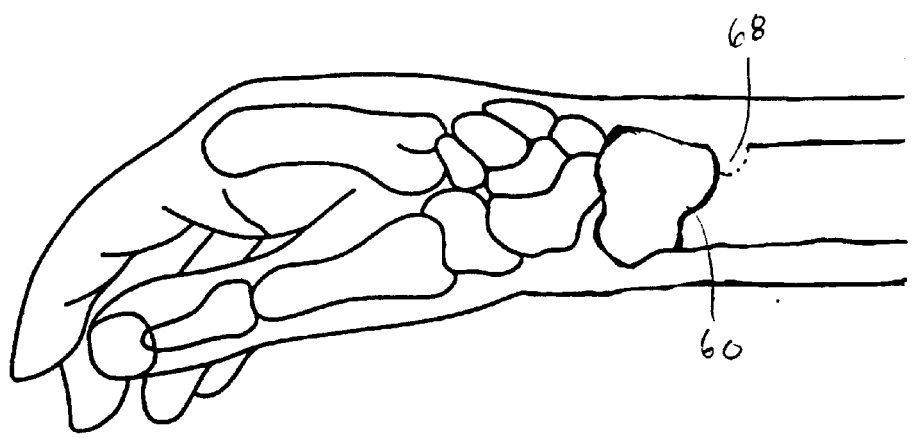
Figure 11:
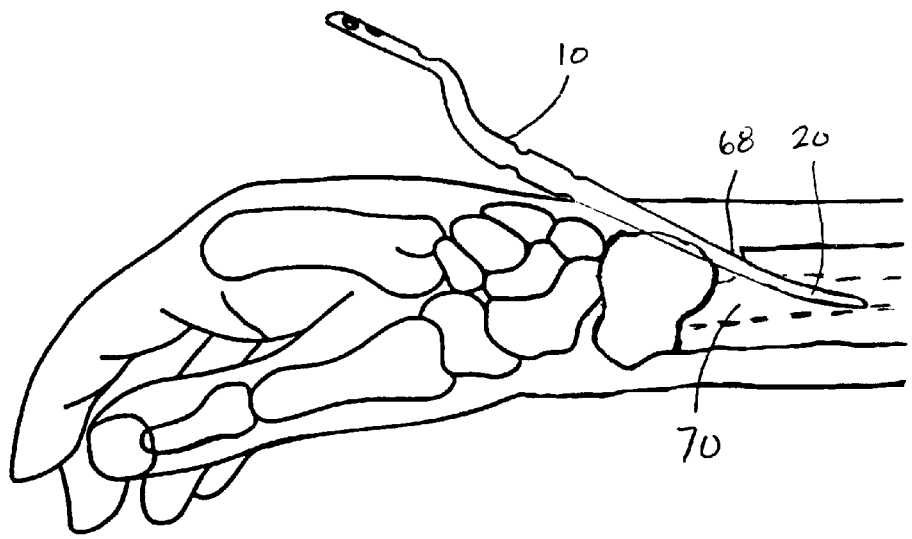

The device 10 is used as follows to treat a fracture 60 of the distal radial bone 62 (e.g., a Colles' fracture), as represented in FIG. 8. Referring to FIG. 9, first, a small incision 64 (generally less than 2 cm) is made in the skin 66 on the dorsal side of the fracture 60. For distal radial fractures, the incision is preferably at a location between the second and third extensor compartments and above Lister's tubercule 67 (a small bump a the distal end of the radius bone) so that the extensor tendons are not irritated by the incision or by the implanted device 10. Referring to FIG. 10, a rongeur (not shown) is then used to take small bites out of the bone at the broken end of the radius bone so that a notch 68 is created preferably on the proximal side of the distal radius fracture 60. In addition, at least a portion of Lister's tubercule is removed to provide s surface for placement of the plate portion 14 at a location which will not cause tendon irritation.

Figure 12:
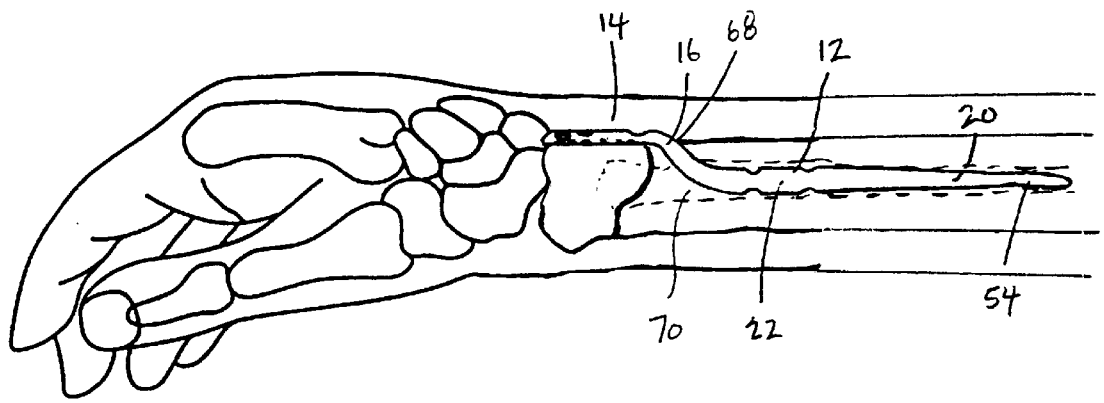

Referring to FIG. 12, the tapered flexible section 20 of the nail portion 12 of the device is then introduced percutaneously through the notch 68 and into the medullary canal 70 of the bone. The nail portion 12 is pushed into the medullary canal 70 of the radius bone 62 until the neck portion 16 lies in the notch 68 created in the distal end of the bone and the plate portion 14 is positioned on the bone distal of the fracture and at the surface of the removed portion of Lister's tubercule. It is appreciated that reduction of the fracture (from the bone position of FIG. 8 to the bone position of FIGS. 9 through 14) may occur at this stage or at any other medically reasonable time during the fracture fixation process. During introduction into the bone and when implanted in the bone, the flexible section 20 of the nail portion 12 will undoubtedly undergo some degree of bending, as the medullary canal may not be perfectly straight and as the nail portion is bent at an angle. As such, the nail portion 12 operates to provide three point fixation along the canal, with the proximal end 54 of the flexible section 20, the bent portion, and the distal rigid section 22 contacting the wall of the medullary canal 70 of the bone. Moreover, the rigid section 22 of the nail portion 12 provides a rigid intramedullary truss which enhances device stabilization.

Figure 13:
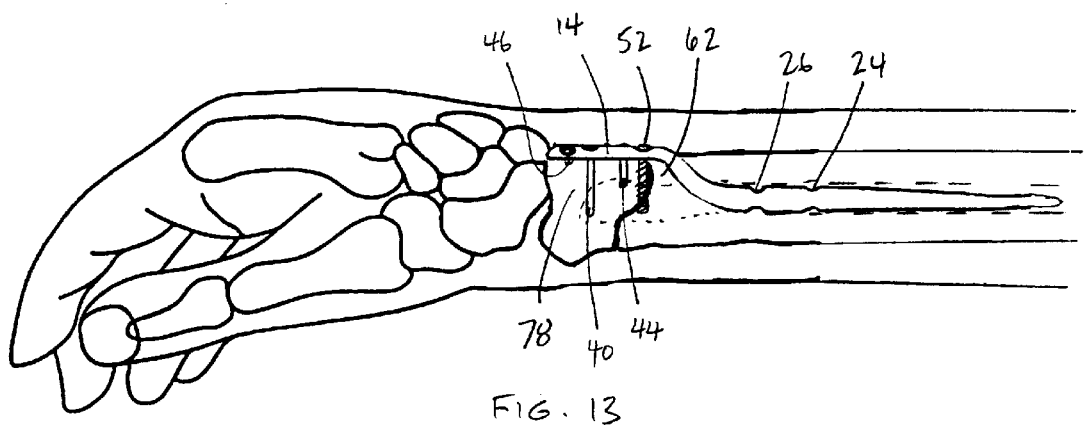

Referring now to FIG. 13, a hole is then drilled into the bone 62 in alignment with the stabilization screw hole 50 and a stabilization screw 52 is used to drive the plate portion 14 up against the bone. With the plate portion 14 stabilized by the screw 52, holes are then drilled into the subchondral bone 78 through peg holes 34, 36, 38 (See FIG. 4). The pegs 40, 44, 46 are then introduced into the peg holes and the holes drilled in the bone. The pegs 40, 44, 46 provide a framework for stabilization and support of bone fragments, including the radial styloid and the volar dipunch, that is particularly effective in view of the fanned orientation of the pegs which follows the subchondral anatomy. Referring back to FIGS. 6 and 7, while the pegs preferably each have a threaded head 48 for engagement within the threaded peg holes, the shafts 49 of the pegs may be either threaded or substantially smooth. Moreover, omnidirectional pegs, such as described in detail in previously incorporated U.S. Ser. No. 09/735,228, may also be used to provide a highly adjustable and customizable framework for bone fragment stabilization. Briefly, the omnidirectional pegs are each inserted into a respective peg hole, and are then be oriented into desired orientation within a permitted range. The pegs are then locked in the desired orientation, e.g., with a set screw.

Figure 14:
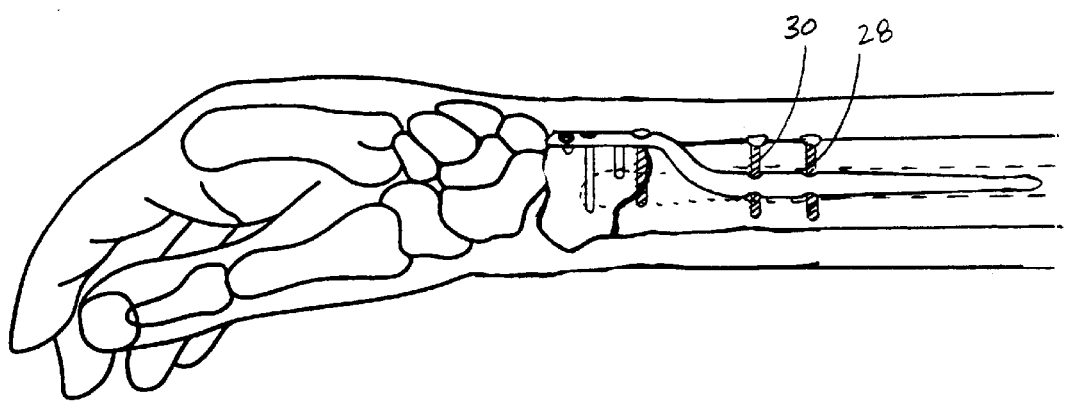

According to a practice well known with respect to intramedullary nails, a guide is then used to locate the positions for the screw holes 24, 26 in the nail portion 12 (FIG. 13). Referring to FIG. 14, at least one of the screws 28, 30 is preferably inserted through puncture holes in the skin, into the bone, and into screw holes 24, 26 to further fixate the device.

It will be appreciated that a device having such features as described can be similarly used to treat other metaphyseal fractures of long bones, e.g., tibial fractures, or combinations of metaphyseal and diaphyseal fractures.

The device provides the benefits of both an intramedullary nail and a bone plate in a single device. The fixation device further permits a minimally invasive treatment of long bone fractures that may otherwise be undertreated.

When the device is used to treat a distal radial fracture, such as a Colles' fracture, particular dimensions are preferred, though the dimensions of the device are not limited thereto. Such preferred dimensions include an overall length of approximately 4.2 inches, the nail portion has a length of approximately 3.56 inches, the plate portion has a length of approximately 0.65 inch, the bottom surface of the plate portion is preferably located approximately 0.29 inch above a longitudinal axis extending through the nail portion. It will be appreciated that the device may be provided in other relative dimensions for the treatment of other metaphyseal bone fractures, such as in the tibia.

There have been described and illustrated herein embodiments of a fixation device and a method of using the device to treat bone fractures. While particular embodiments of the invention have been described, it is not intended that the invention be limited thereto, as it is intended that the invention be as broad in scope as the art will allow and that the specification be read likewise. Thus, while particular dimensions have been disclosed, it will be appreciated that other dimensions may be used as well. In addition, while titanium and stainless steel are the preferred materials, it will be understood that other biocompatible materials can be used. Moreover, the flexible portion may be made from a different material than the rigid portion, and the two portions may then be joined. Also, while the pegs are preferably fanned at 45° relative to each adjacent peg, other fanned arrangements can be used. It will therefore be appreciated by those skilled in the art that yet other modifications could be made to the provided invention without deviating from its spirit and scope as claimed.

What is claimed is:

1. A bone fracture fixation device, comprising:
   a) a tapered nail portion including two longitudinally displaced screw holes; and
   b) a relatively flatter plate portion provided with at least one threaded peg hole.

2. A bone fracture fixation device comprising:
   a) a tapered nail portion including at least one screw hole; and
   b) a relatively flatter plate portion provided with at least one threaded peg hole, said plate portion including three longitudinally displaced peg holes.

3. A bone fracture fixation device, comprising:
   a) a tapered nail portion including at least one screw hole; and
   b) a relatively flatter plate portion provided with at least one threaded peg holes
      wherein said nail portion and said plate portion are substantially parallel and non-coaxial.

4. A bone fracture fixation device according to claim 3, wherein:
   said plate portion has a concave lower surface and a convex upper surface.

5. A bone fracture fixation device, comprising:
   a) an elongate nail portion having a relatively stiff and non resilient portion; and
   b) a longitudinally displaced relatively flatter plate portion being non-coaxial with said nail portion, said plate portion including at least one hole with a threaded portion said plate portion extending parallel to said relatively stiff and non-resilient portion of said nail portion.

6. A bone fracture fixation device according to claim 5, wherein:
   said nail portion has a circular cross-section.

7. A bone fracture fixation device comprising:
   a) an elongate nail portion having a relatively stiff and non resilient portion; and
   b) a longitudinally displaced relatively flatter plate portion being non-coaxial with said nail portion, said plate portion including at least one hole with a threaded portion, said plate portion including a plurality of holes, each said hole including a threaded portion.

8. A bone fracture fixation device according to claim 7, wherein:
   said holes each have an axis which is provided in a distinct orientation relative to the other axes.

9. A bone fracture fixation device according to claim 7, wherein:
   said plate portion includes at least three holes, and said holes are longitudinally displaced along said plate portion.

10. A bone fracture fixation device for use with a plurality of pegs each having a threaded head portion, said device comprising:
    a) an elongate nail portion;
    b) a longitudinally displaced plate portion having upper and lower surfaces which are each non-planar, said plate portion defining three threaded peg holes; and
    c) a plurality of pegs each having a threaded head portion, wherein said threaded peg holes define axes adapted to provide said pegs inserted into said peg holes in an arrangement in which at least two of said pegs extend in discrete directions.

11. A bone fracture fixation device according to claim 10, wherein:
    said peg holes are arranged such that each of said pegs extends in a discrete direction.

12. A bone fracture fixation device for use in a bone having a diaphyseal portion and a metaphyseal portion and having a fracture at or adjacent the metaphyseal portion, said device comprising:
    a) a nail portion provided with means for fixing said nail portion to the diaphyseal portion of bone; and
    b) a plate portion defining a threaded peg hole adapted to receive a peg having a head with corresponding threads such that the peg can be received into the threaded peg hole in alignment with a single axis.

13. A bone fracture fixation device according to claim 12, further comprising:
    c) at least one peg with a threaded head portion.

14. A bone fracture fixation device according to claim 12, wherein:
    said means for fixing includes two longitudinally displaced holes.

15. A bone fracture fixation device according to claim 12, wherein:
    said plate portion includes three threaded peg holes, the holes being arranged such that pegs received in said threaded peg holes are aligned in oblique directions relative to each other.

16. A bone fracture fixation device, comprising:
    a) an elongate nail portion including a relatively flexible section and a relatively rigid section relatively larger in diameter than said relatively flexible section; and
    b) a plate portion including a plurality of threaded peg holes, said plate portion being parallel to but not coaxial with said nail portion.

17. A bone fracture fixation device according to claim 16, wherein:
    said relatively rigid section of said nail portion is substantially straight.

18. A bone fracture fixation device according to claim 1, wherein:
    said relatively flexible section is sized to be inserted into a medullary canal of a radius bone.

19. A bone fracture fixation device according to claim 16, wherein:
    said nail portion is substantially circular in cross section.

20. A bone fracture fixation device according to claim 16, wherein:
    said relatively flexible section has a tapered diameter along its length.

21. A bone fracture fixation device according to claim 16, wherein:
    said relatively rigid section tapers in diameter into said relatively flexible section portion.

22. A bone fracture fixation device according to claim 16, wherein:
    said nail portion includes at least one screw hole.

23. A bone fracture fixation device according to claim 16, wherein:
    said peg holes are longitudinally displaced along said plate portion.

24. A bone fracture fixation device according to claim 16, wherein:
said peg holes are each oriented in a discrete direction.

25. A bone fracture fixation device according to claim 24, further comprising:
c) a plurality of pegs, each having a threaded head portion which is threaded in one of said threaded peg holes.

26. A bone fracture fixation device according to claim 16, wherein:
said plate portion is longitudinally offset relative to said nail portion by a neck portion.

27. A bone fracture fixation device according to claim 15, wherein:
said neck portion has an 'S' shape.

28. A bone fracture fixation device according to claim 16, wherein:
said relatively flexible section of said nail portion is laterally angled relative to a distal portion of said rigid section of said nail portion.

29. A bone fracture fixation device according to claim 16, wherein:
said plate portion includes a substantially concave lower surface.

30. A bone fracture fixation device according to claim 16, wherein:
said plate portion includes a substantially convex upper surface.

31. A bone fracture fixation device according to claim 16, wherein:
said relatively rigid section of said nail portion includes at least one screw hole.

32. A bone fracture fixation device for use with a plurality of pegs each having a threaded head portion, said device comprising:
a) an elongate nail portion; and
b) a longitudinally displaced relatively flatter plate portion including a plurality of longitudinally displaced threaded peg holes, said peg holes having axes adapted to provide the pegs inserted into said peg holes in an arrangement in which at least two of the pegs extend in discrete directions.

33. A bone fracture fixation device according to claim 32, wherein:
said plate portion is horizontally and vertically offset relative to said nail portion.

34. A bone fracture fixation device according to claim 32, wherein:
said nail portion includes a relatively flexible section and a relatively rigid section relatively larger in diameter than said relatively flexible section.

35. A bone fracture fixation device according to claim 32, wherein:
said peg holes are arranged such that each of said pegs extends in a discrete direction.

36. A bone fracture fixation device according to claim 32, wherein:
said nail portion includes at least one screw hole.

37. A bone fracture fixation system, comprising:
a) a fixation device including
   i) an elongate nail portion, and
   ii) a relatively flatter plate portion including a plurality of longitudinally displaced peg holes,
   said plate portion being horizontally and vertically offset relative to said nail portion;
b) a plurality of pegs individually insertable into a respective one of said peg holes,
   wherein when each said peg is inserted into its respective peg hole, said peg can be oriented in any of several orientations; and
c) means for locking each said peg in any of its orientations.

38. A bone fracture fixation device according to claim 32, wherein
said nail portion includes a relatively flexible section and a relatively rigid section relatively larger in diameter than said relatively flexible section.

* * * * *